United States Patent
Chiang (10) Patent No.: US 8,826,924 B2
(45) Date of Patent: Sep. 9, 2014

(54) FLOSS HOLDER

(71) Applicant: Ming-Chia Chiang, Changhua (TW)

(72) Inventor: Ming-Chia Chiang, Changhua (TW)

(*) Notice: Subject to any disclaimer, the term of this patent is extended or adjusted under 35 U.S.C. 154(b) by 0 days.

(21) Appl. No.: 13/687,939

(22) Filed: Nov. 28, 2012

(65) Prior Publication Data

US 2014/0144461 A1    May 29, 2014

(51) Int. Cl.
*A61C 15/00* (2006.01)
*A61C 15/04* (2006.01)

(52) U.S. Cl.
CPC .................. *A61C 15/041* (2013.01)
USPC ........................................................ 132/323

(58) Field of Classification Search
USPC ................................................ 132/322–329
See application file for complete search history.

(56) References Cited

U.S. PATENT DOCUMENTS

| | | | | |
|---|---|---|---|---|
| 1,050,469 A * | 1/1913 | Keifer | ............................ | 433/142 |
| 1,180,620 A * | 4/1916 | Stuart | ............................ | 132/324 |
| 2,784,722 A * | 3/1957 | Chamberlin et al. | .......... | 132/324 |
| 4,615,349 A * | 10/1986 | Kukuruzinski | ............... | 132/323 |
| 2013/0160790 A1 * | 6/2013 | Yap | ................................ | 132/324 |

* cited by examiner

*Primary Examiner* — Rachel Steitz
(74) *Attorney, Agent, or Firm* — Muncy, Geissler, Olds & Lowe, P.C.

(57) ABSTRACT

A floss holder includes a holder body having two suspension arms, a shaft joining the suspension arms and a through hole at a front end of each suspension arm, and two rivets respectively mounted in the through holes each having factory head disposed outside one end of one through hole, and a floss-retaining unit defined between the factory head and one respective suspension arm for securing a dental floss.

5 Claims, 11 Drawing Sheets

FLOSS HOLDER

BACKGROUND OF THE INVENTION

1. Field of the Invention

The present invention relates tooth cleaning tools and more particularly, to a floss holder capable of holding a dental floss positively in a highly stretched condition for application.

2. Description of the Related Art

Figure 1:
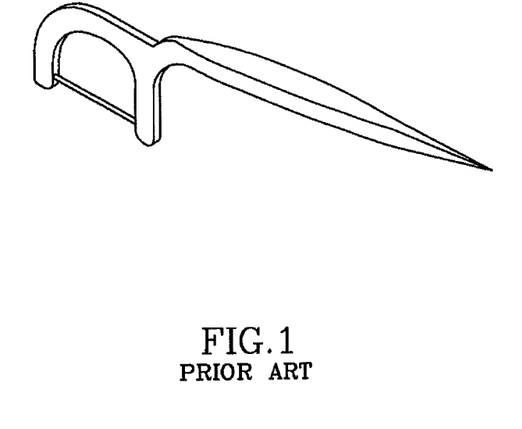
FIG. 1 is an elevational view of a disposable floss pick according to the prior art.
Figure 2:
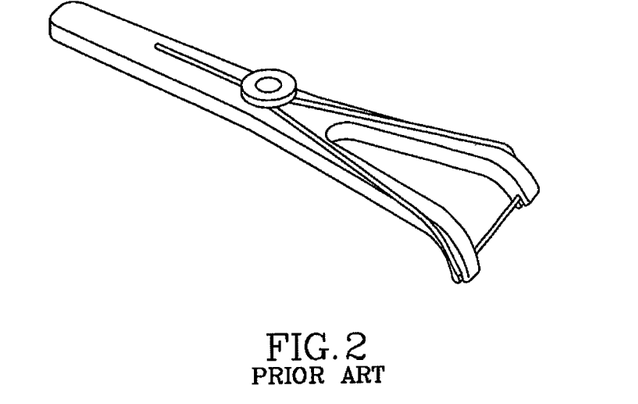
FIG. 2 is an elevational view of a floss holder according to the prior art.
Figure 3:
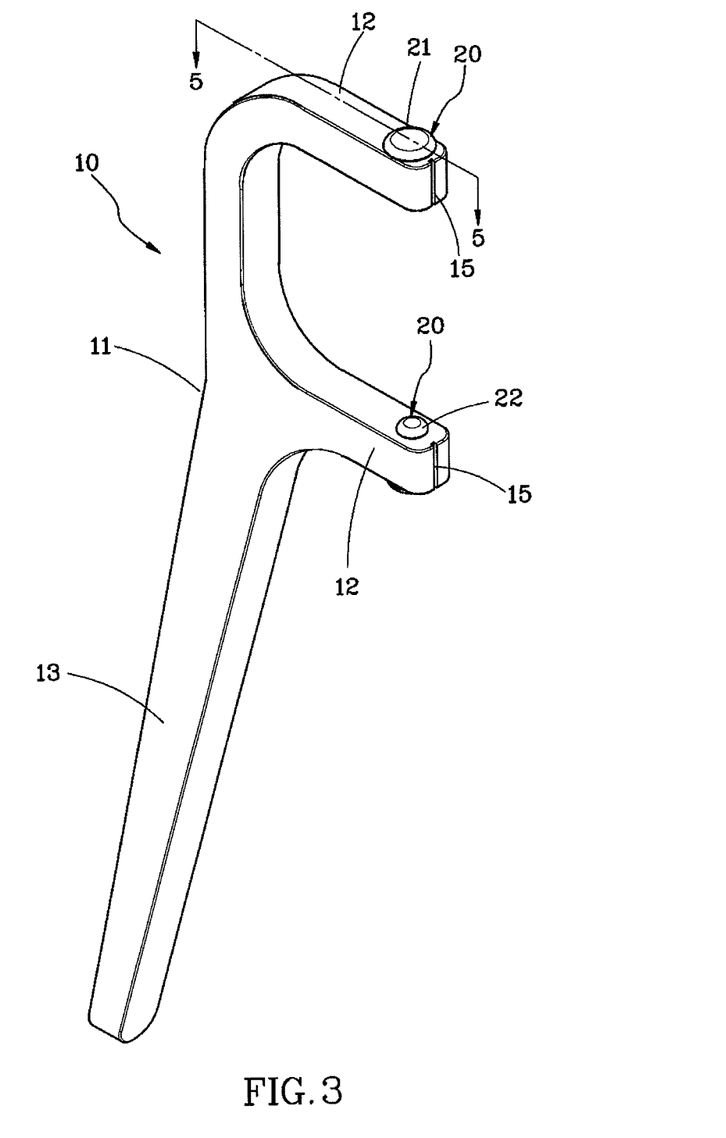
FIG. 3 is an elevational view of a floss holder in accordance with a first embodiment of the present invention.

Disposable and floss-winding type floss picks are commercially available. A disposable floss pick, as shown in FIG. 1, is a disposable oral hygiene device generally made of plastic and dental floss in integrity. This kind of disposable floss pick has the drawback of low level of floss tension. During application, it is difficult to insert the dental floss into a narrow gap between teeth. When forcing the dental floss into a narrow gap with force, the dental floss may break. If the dental floss is broken or damaged, the disposable floss pick becomes useless and must be replaced. When cleaning the teeth after a meal, one disposable floss pick may be not insufficient. It is expensive to clean the teeth with multiple disposable floss picks after each meal. Further, using this kind of disposable floss pick to clean, the teeth is less comfort. Therefore, this kind of disposable floss pick is suitable for temporary use only when one goes out. A floss-winding type floss pick, as shown in FIG. 2, generally comprises a Y-shaped pick body having a shaft, two arms extended from one end of the shaft and a notch located at the distal end of each arm, and a floss-winding member located at the shaft adjacent to the arms. During application, pick up a piece of dental floss, and then wind one end of the piece of dental floss round the floss-winding member, and then extend the piece of dental floss through the notch at each arm, and then wind the other end of the piece of dental floss round the floss-winding member again. Thus, the piece of dental floss is stretched between the two arms for application. According to this design of floss-winding type floss pick, a certain length of dental floss must be used for each application. In consequence, the consumption of dental floss is faster. Further, the positioning of the installed dental floss is not accurately fixed, and the installed dental floss may be loosened during application. Further, because the Y-shaped pick body of floss-winding type floss pick is made out of a plastic material, the structural strength of the suspension arms is weak. In consequence, the installed dental floss is not highly stretched. Further, this design of floss-winding type floss pick has a large dimension. It is suitable for home use only, not suitable for use in outdoor public places.

SUMMARY OF THE INVENTION

The present invention has been accomplished under the circumstances in view. It is the main object of the present invention to provide a floss holder, which can hold a dental floss positively in a highly stretched condition for application to impart a high level of comfort.

It is another object of the present invention to provide a floss holder, which minimizes floss waste.

It is still another object of the present invention to provide a floss holder, which has a compact size, convenient for carrying.

To achieve these and other objects of the present invention, a floss holder comprises a holder body and two rivets. The holder body comprises two suspension arms, a shaft joining the two suspension arms, and a through hole at a front end of each suspension arm. The two rivets are respectively inserted through the through holes, each comprising a factory head disposed outside one end of the respective through hole, and a floss-retaining unit defined between the factory head and the respective suspension arm for securing a dental floss.

DETAILED DESCRIPTION OF THE INVENTION

Referring to FIGS. 3-6, a floss holder 10 in accordance with a first embodiment of the present invention is shown. As illustrated, the floss holder 10 comprises a holder body 11 and two rivets 20.

The holder body 11 comprises two suspension arms 12, and a shaft 13 joining the suspension arms 12. Each suspension arm 12 defines a through hole 14 and a floss guide groove 15 at a front end thereof. In this embodiment, the two through holes 14 are aligned on one same axis, and the two floss guide grooves 15 are aligned on another axis.

The two rivets 20 are respectively mounted in the aforesaid two through holes 14, each comprising a factory head 21 disposed outside an outer end of the respective through hole 14 and a buck-end 22 bucked and stopped outside an opposite inner end of the respective through hole 14. Thus, a floss-retaining unit 16 is defined between the factory head 21 of each rivet 20 and the corresponding suspension arm 12 of the holder body 11.

Figure 4:
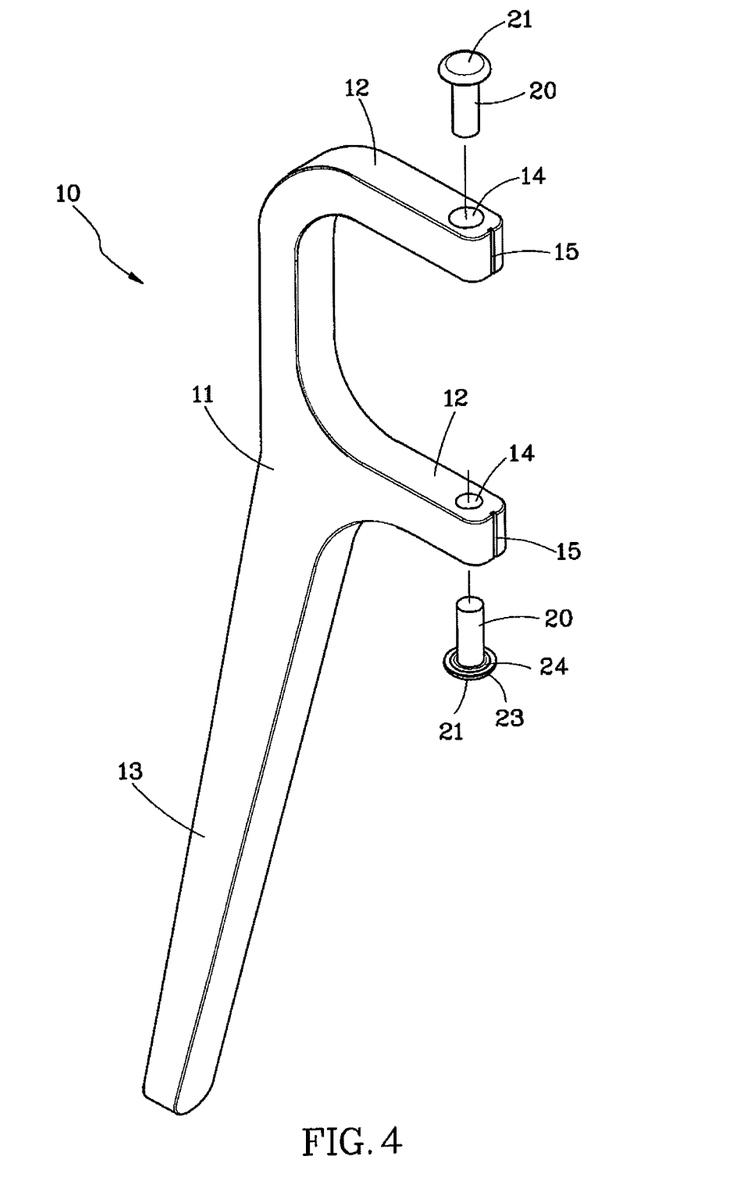
FIG. 4 is an exploded view of the floss holder in accordance with the first embodiment of the present invention.
Figure 5:
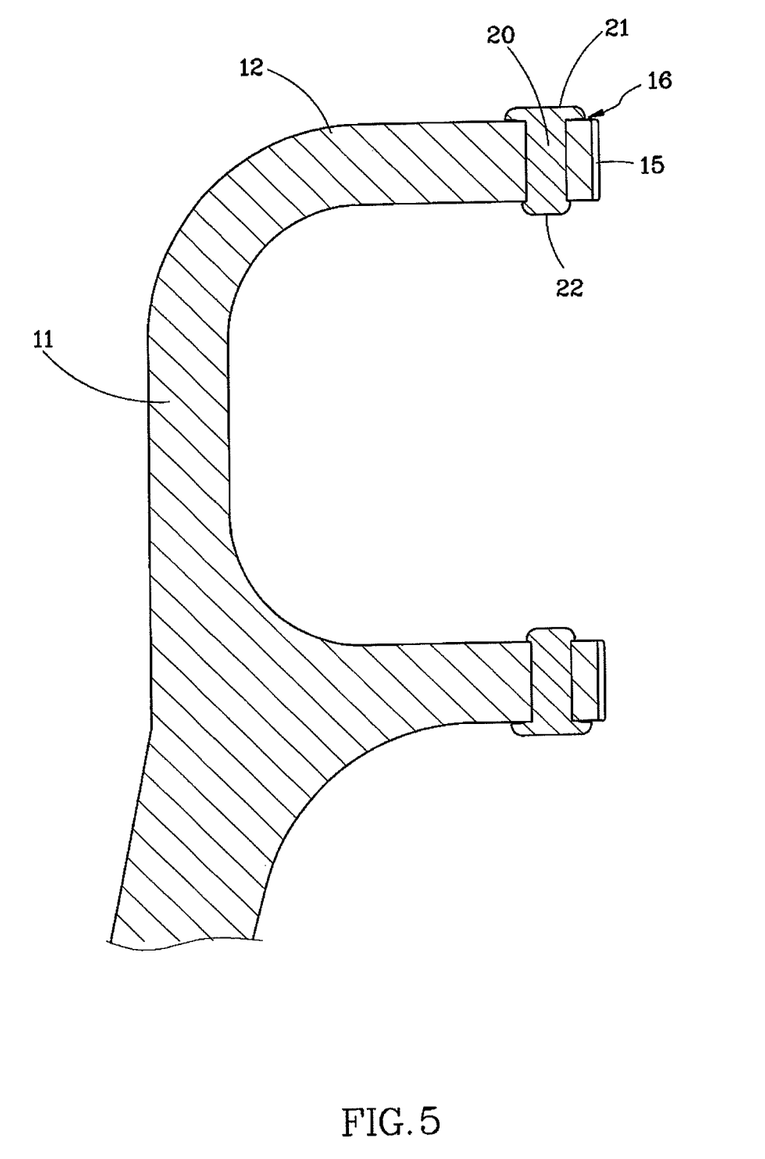
FIG. 5 is a sectional view taken along line 5-5 of FIG. 3.
Figure 6:
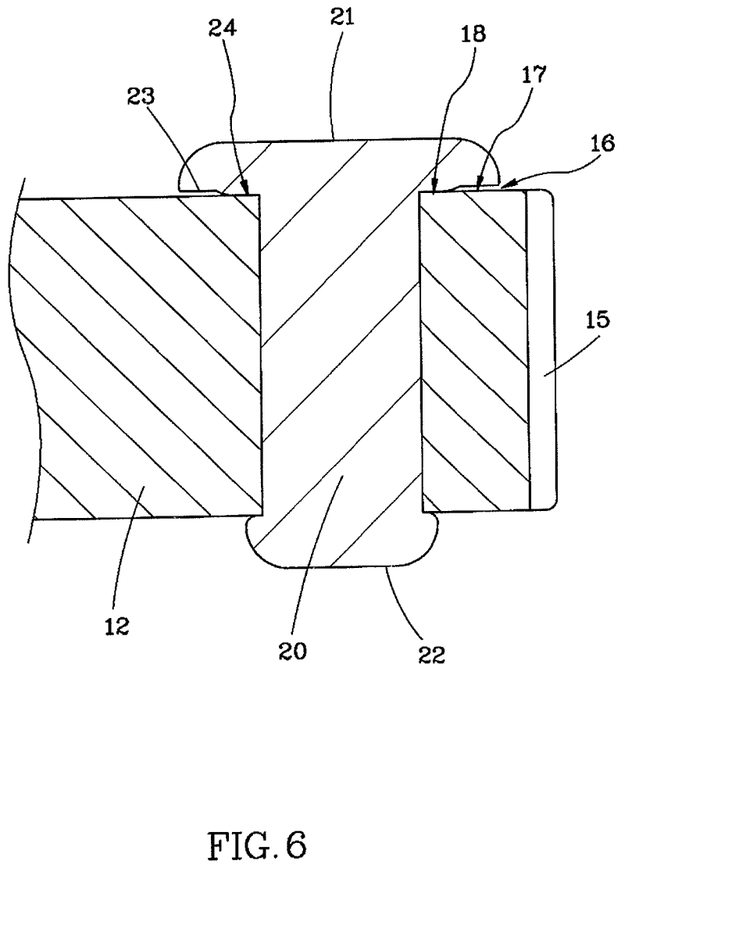
FIG. 6 is an enlarged view of a part of FIG. 5.
Figure 7:
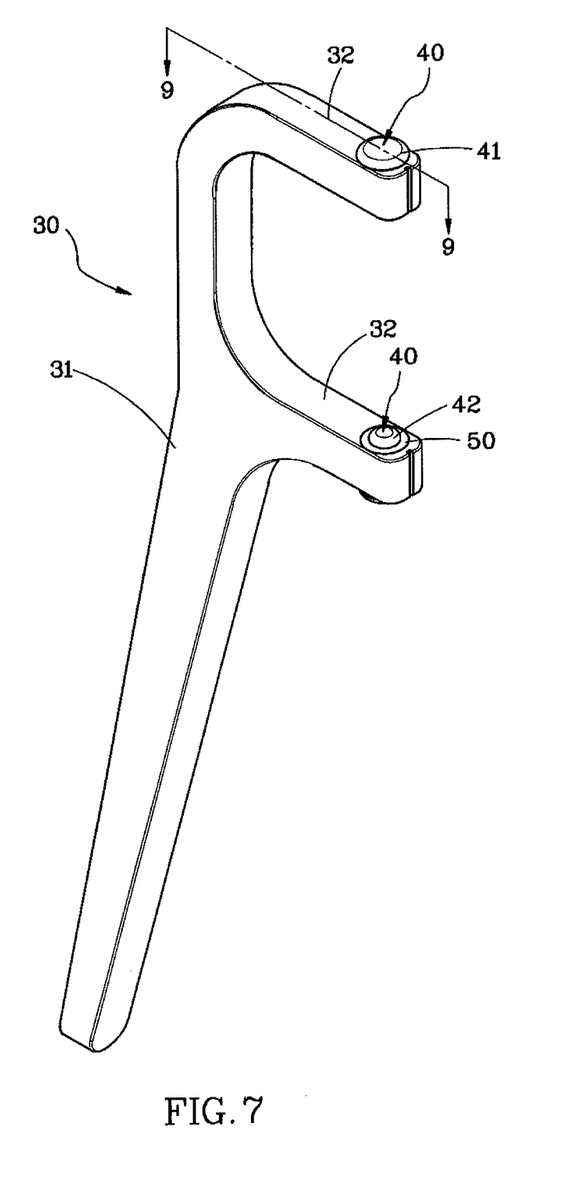
FIG. 7 is an elevational view of a floss holder in accordance with a second embodiment of the present invention.
Figure 8:
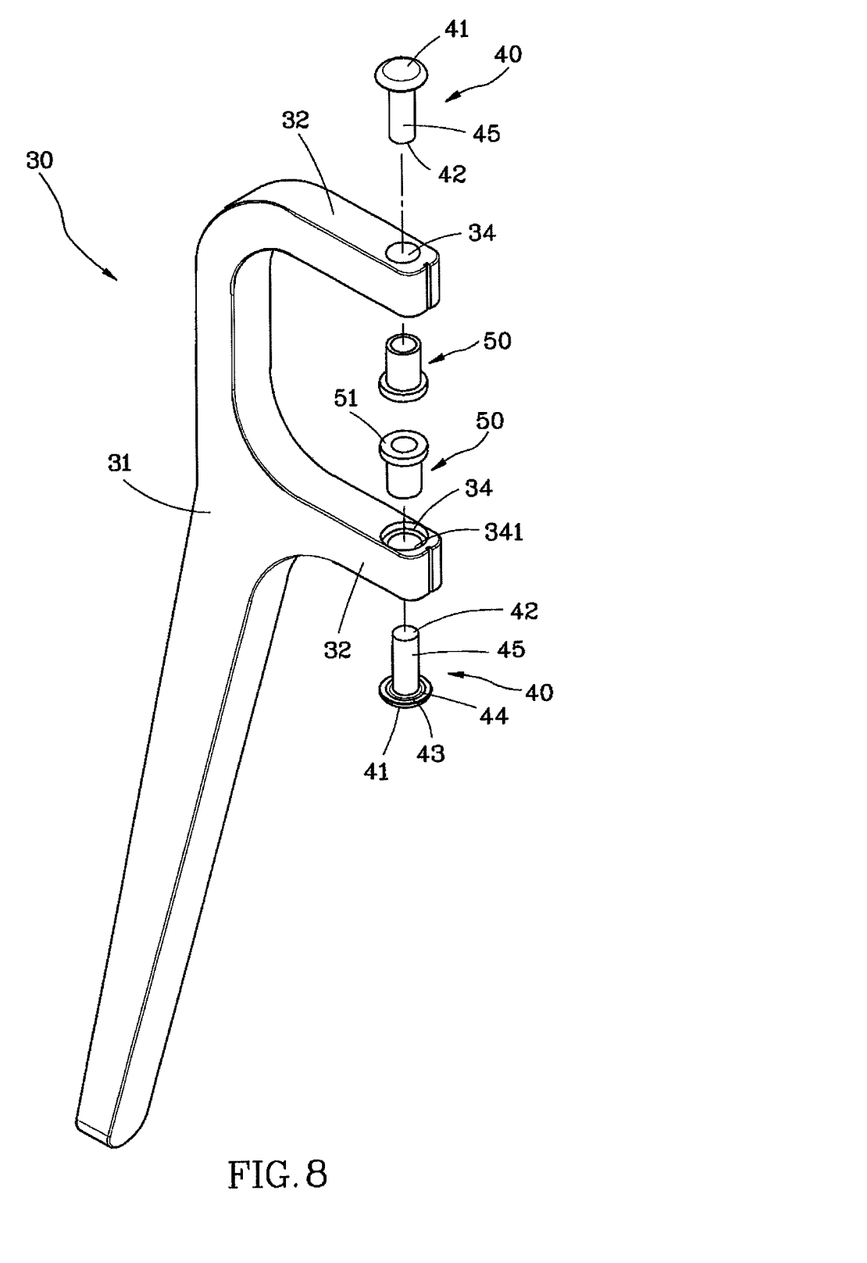
FIG. 8 is an exploded view of the floss holder in accordance with the second embodiment of the present invention.
Figure 9:
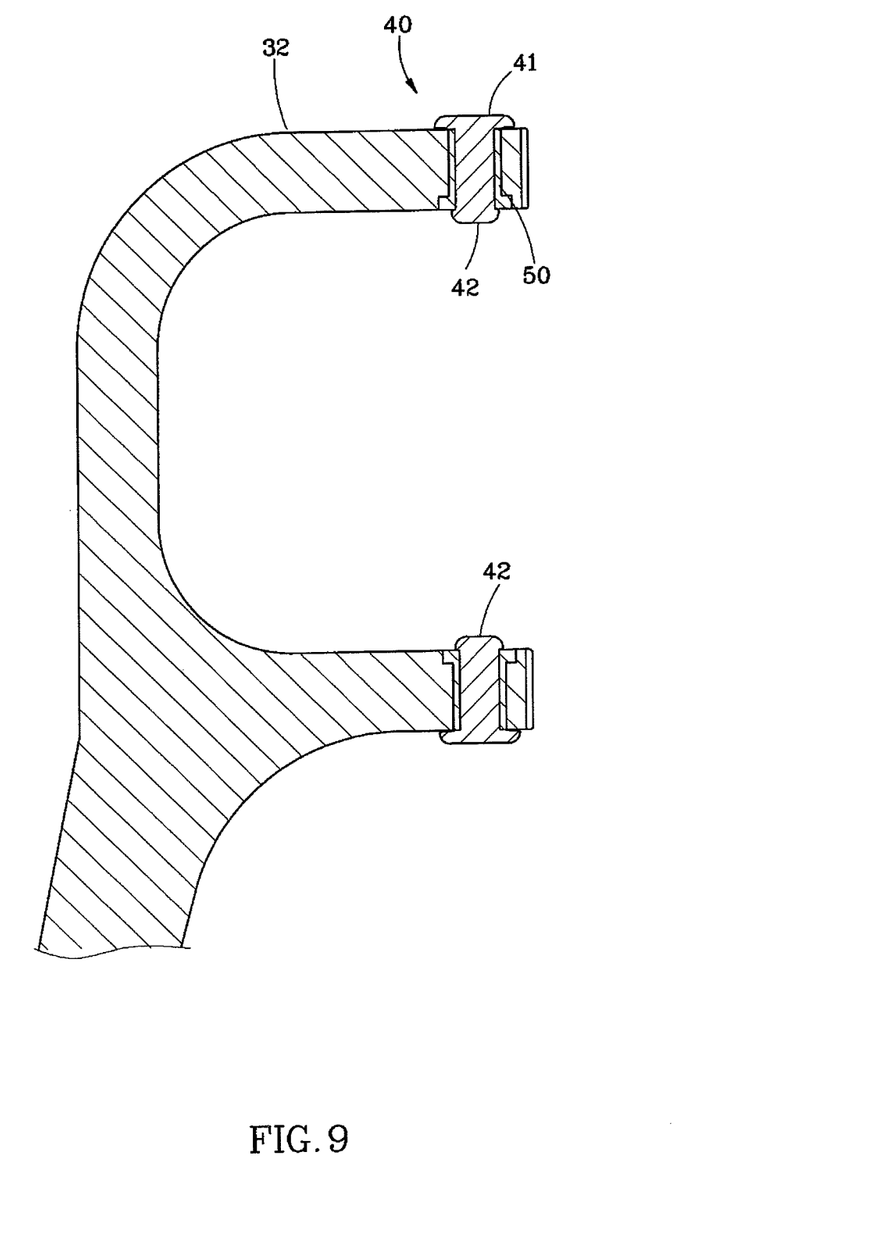
FIG. 9 is a sectional view taken along line 9-9 of FIG. 7.

The factory head 21 of each rivet 20 has a stepped inner side defining an outer terrace 23 and an inner terrace 24 (see FIG. 4). The inner terrace 24 is raised from the outer terrace 23. Thus, the stepped inner side of the factory head 21 of each rivet 20 divides the respective floss-retaining unit 16 into an outer floss-guide portion 17 and an inner floss-retaining portion 18 (see FIG. 6).

During application, wind a lead end of a small piece of floss round the floss-retaining unit 16 of one rivet 20 at one suspension arm 12 to have the lead end of the small piece of floss be guided through the respective floss-guided portion 17 and secured to the respective floss-retaining portion 18, and then extend the small piece of floss through the floss guide groove 15 of this suspension arm 12 and the floss guide groove 15 of the other suspension arm 12, and then wind an opposite tail end of the small piece of floss round the floss-retaining unit 16 of the other rivet 20 to have the tail end of the small piece of floss be guided through the floss-guided portion 17 of the floss-retaining unit 16 and secured to the floss-retaining portion 18 of the floss-retaining unit 16. After the use of the installed floss, reverse the aforesaid procedure to remove the used floss from the floss holder 10 rapidly and conveniently. This design of floss holder 10 can hold a small piece of floss positively in position for application.

It is to be noted that the floss holder utilizes the small clearance between each rivet and the corresponding suspension arm and stretching and displacement flexibility between each rivet and the corresponding suspension arm to secure the loaded floss in place for application, and therefore the rivets and the suspension arms are preferably made of materials of different hardness, for example, one made of engineering plastics and the other made of metal (according to this first embodiment, the holder body 11 is made out of a plastic material, and the rivets 20 are made of metal). Alternatively, the rivets and the suspension arms can be made of different metals of different hardness, for example, one made of steel and other made of copper. In short, the present invention utilizes the material resilient property to provide a holding down force and a friction force to secure the dental floss in place.

From the above description, it is apparent that the floss holder can get better stiffness to highly stretch the dental floss if both the holder body and the rivets are made of metal. However, if both the floss holder and the rivets are made of metals, the low level of compression elasticity between the holder body and the rivets may cause the loaded dental floss unable to be firmly secured in place. In order to eliminate this problem, the invention provides a plastic bushing between each rivet and the corresponding suspension arm. By means of the elastic material property of the plastic bushings, the floss holder provides better floss-retaining flexibility.

FIGS. 7-10 illustrate a floss holder 30 in accordance with a second embodiment of the present invention. According to this second embodiment, the floss holder 30 comprises a holder body 31, two rivets 40, and two bushings 50 respectively mounted in the through holes 34 of the suspension arms 32 of the holder body 31 around the rivets 50.

Figure 10:
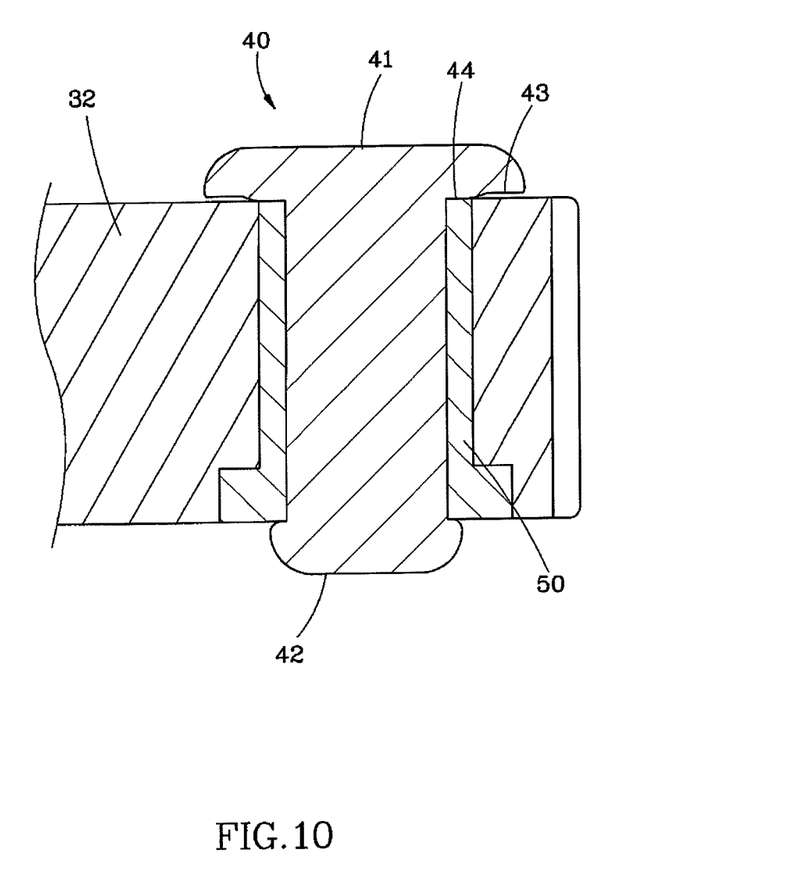
FIG. 10 is an enlarged view of a part of FIG. 9.

The bushings 50 are shaped like a flanged tube, each having a flange 51 extending around the outer perimeter of one end thereof. The rivets 40 are respectively inserted through the bushings 50. The through holes 34 are countersunk holes, each having an expanded accommodation portion 341 at one end thereof for accommodating the flange 51 of the respective bushing 50. During installation, each rivet 40 is inserted with the shank 45 thereof from one bushing 50 to let its head 41 stopped at the other end (the plain end) of rivet 40 and its bush-tail 42 suspending outside the flange 51 of the respective bushing 50, and then the buck-ended is bucked and stopped outside the flange 51 of the respective bushing 50. As illustrated in FIG. 10, the buck-end 42 of each rivet 40, after having been bucked, is kept in direct contact with the respective bushing 50 and spaced from the holder body 31 at a distance with the inner terrace 44 of the factory head 41 thereof almost wholly kept in contact with the respective bushing 50 and the outer terrace 43 thereof kept beyond the respective bushing 50. This design allows the holder body 31 and the rivets 40 to be both made of metal. By means of the elastic material property of the plastic material of the bushings 50, each rivet 40 and the respective bushing 50 can be moved slightly and axially relative to each other for enabling the dental floss to be forced in between each rivet 40 and the respective bushing 50 and positively secured in place by each rivet 40 and the respective bushing 50.

Figure 11:
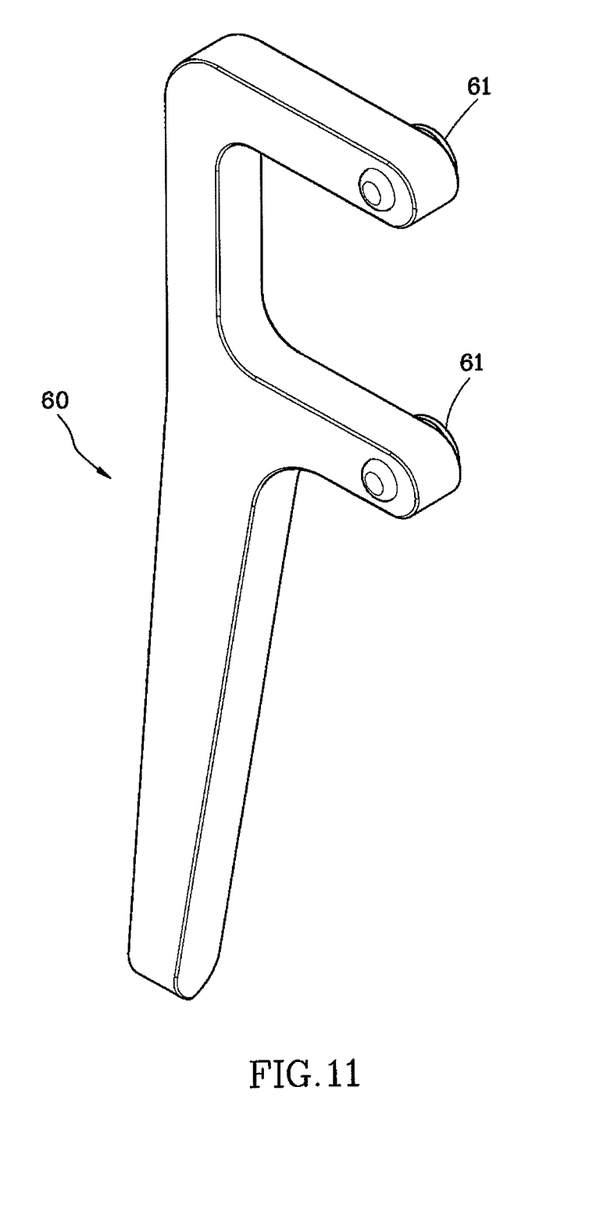
FIG. 11 is an elevational view of a floss holder in accordance with a third embodiment of the present invention.

FIG. 11 illustrates a floss holder 60 in accordance with a third embodiment of the present invention. According to this third embodiment, the floss holder 60 has a substantially F-shaped profile without the aforesaid floss guide grooves and with the two rivets 61 thereof arranged in parallel.

Figure 12:
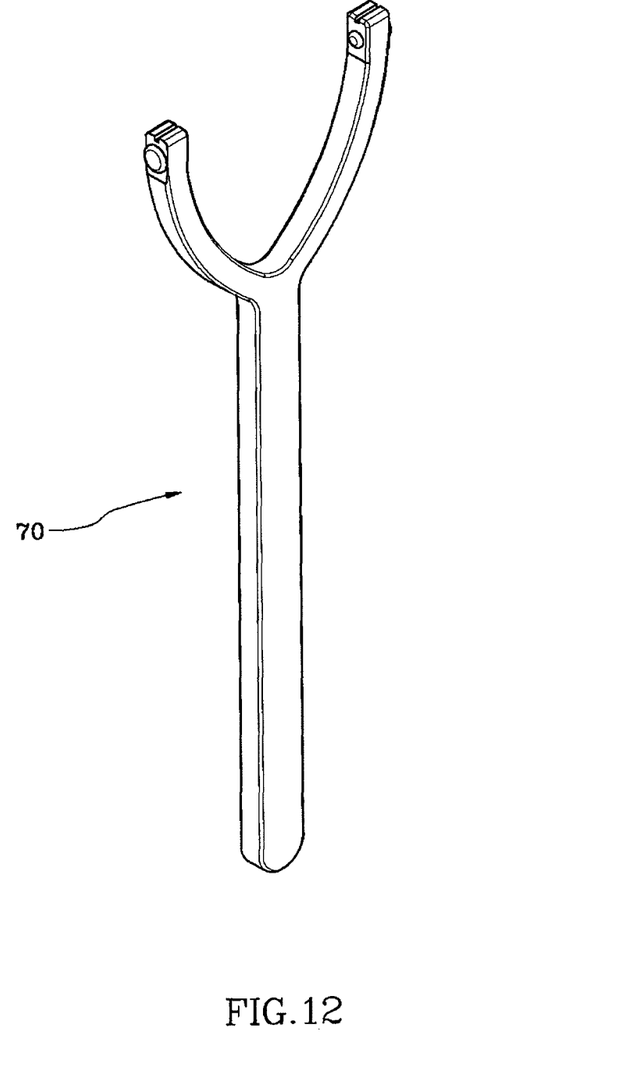
FIG. 12 is an elevational view of a floss holder in accordance with a fourth embodiment of the present invention.

FIG. 12 illustrates a floss holder 70 in accordance with a fourth embodiment of the present invention. This fourth embodiment is substantially similar to the aforesaid second embodiment with the exception that the floss holder 70 of this fourth embodiment has a substantially Y-shaped profile.

Although particular embodiments of the invention have been described in detail for purposes of illustration, various modifications and enhancements may be made without departing from the spirit and scope of the invention. Accordingly, the invention is not to be limited except as by the appended claims.

What is claimed is:

1. A floss holder, comprising:
a holder body comprising two suspension arms and a shaft joining said two suspension arms, each said suspension arm comprising a through hole at a front end thereof;
two rivets respectively inserted through said through holes, each said rivet comprising a factory head disposed outside one end of one said through hole, a buck-end being hammered down and suspending outside an opposite end of the respective said through hole, and a floss retaining unit defined between said factory head and one respective said suspension arm for securing a dental floss,
wherein the floss holder utilizes a small clearance between each rivet and the corresponding suspension arm and stretching and displacement flexibility between each rivet and the corresponding suspension arm to secure the loaded floss in place for application, and
wherein the factory head of each said rivet comprises a stepped inner side defining an outer terrace and an inner terrace raised from said outer terrace, said stepped inner side dividing said floss-retaining unit into an outer floss-guide portion and an inner floss-retaining portion.

2. The floss holder as claimed in claim 1, wherein each said suspension arm defines a floss guide groove at a front edge thereof.

3. The floss holder as claimed in claim 1, further comprising two bushings respectively mounted in said holder body around said rivets,
wherein said through hole runs through said bushing.

4. The floss holder as claimed in claim 3, wherein said rivets and said bushings are made of materials of different hardness.

5. The floss holder as claimed in claim 3, wherein each said through hole has an expanded accommodation portion at one end thereof; each said bushing comprises a flange extending around an outer perimeter of one end thereof and accommodated in said expanded accommodation portion of the respective said through hole.

* * * * *